United States Patent
Kolenbrander et al.

(10) Patent No.: US 9,248,446 B2
(45) Date of Patent: Feb. 2, 2016

(54) SYSTEM FOR BLOOD SEPARATION WITH A SEPARATION CHAMBER HAVING AN INTERNAL GRAVITY VALVE

(71) Applicant: Terumo BCT, Inc., Lakewood, CO (US)

(72) Inventors: Jeremy P. Kolenbrander, Brighton, CO (US); Geoffrey Uhl, Littleton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 14/179,955

(22) Filed: Feb. 13, 2014

(65) Prior Publication Data

US 2014/0234183 A1    Aug. 21, 2014

Related U.S. Application Data

(60) Provisional application No. 61/765,948, filed on Feb. 18, 2013.

(51) Int. Cl.
*B01L 3/00* (2006.01)
*A61M 1/38* (2006.01)
(Continued)

(52) U.S. Cl.
CPC ............ *B01L 3/5021* (2013.01); *A61M 1/0209* (2013.01); *A61M 1/3693* (2013.01);
(Continued)

(58) Field of Classification Search
CPC ............... A61M 1/3693; C12M 47/04; G01N 2035/00495; B01D 21/262; B01D 17/0217
USPC ..................................... 422/533; 494/4; 435/2
See application file for complete search history.

(56) References Cited

U.S. PATENT DOCUMENTS

| | | |
|---|---|---|
| 1,684,870 A | 9/1928 | Lewis |
| 2,616,619 A | 11/1952 | MacLeod |

(Continued)

FOREIGN PATENT DOCUMENTS

| | | |
|---|---|---|
| DE | 2658926 A1 | 6/1978 |
| DE | 3413065 A1 | 10/1984 |

(Continued)

OTHER PUBLICATIONS

Almici, C. et al., "Counterflow Centrifugal Elutriation: Present and Future", Bone Marrow Transplantation, 1993, pp. 105-108, vol. 12, Macmillan Press Ltd.

(Continued)

*Primary Examiner* — Dennis M White
*Assistant Examiner* — Bryan Kilpatrick
(74) *Attorney, Agent, or Firm* — John R. Merkling; Elizabeth J. Reagan; René A. Pereyra

(57) ABSTRACT

A disposable blood separation set and a centrifugal blood processing system comprising a blood processing chamber adapted to be mounted on a rotor of a centrifuge; a frustro-conical cell separation chamber in fluid communication with the processing chamber, the cell separation chamber having an inlet, an outlet and a gravity valve inside the cell separation chamber. The valve is responsive to the gravitational field created by the speed of the rotor. When the rotor spins at high speed, the gravity valve may open the outlet at a location proximal to an axis of rotation of the rotor. When the rotor spins at a lower speed, the gravity valve may open the outlet at a location distal from the axis.

10 Claims, 6 Drawing Sheets

(51) Int. Cl.
  *A61M 1/36* (2006.01)
  *B04B 5/04* (2006.01)
  *A61M 1/02* (2006.01)
  *B01D 21/26* (2006.01)

(52) U.S. Cl.
  CPC .......... *A61M 1/3696* (2014.02); *A61M 1/3698* (2014.02); *A61M 1/38* (2013.01); *B04B 5/0442* (2013.01); *B01D 21/26* (2013.01); *B04B 2005/0471* (2013.01)

(56) References Cited

U.S. PATENT DOCUMENTS

| | | |
|---|---|---|
| 2,878,995 A | 3/1959 | Dega |
| 3,211,368 A | 10/1965 | Shanley |
| 3,559,880 A | 2/1971 | Naito et al. |
| 3,724,747 A | 4/1973 | Unger et al. |
| 3,737,096 A | 6/1973 | Jones et al. |
| 3,761,014 A | 9/1973 | Carter |
| 3,771,715 A | 11/1973 | Baram |
| 3,823,869 A | 7/1974 | Loison |
| 3,825,175 A | 7/1974 | Sartory |
| 3,987,961 A | 10/1976 | Sinn et al. |
| 4,007,871 A | 2/1977 | Jones et al. |
| 4,010,894 A | 3/1977 | Kellogg et al. |
| 4,059,967 A | 11/1977 | Rowe et al. |
| 4,091,989 A | 5/1978 | Schlutz |
| 4,094,461 A | 6/1978 | Kellogg et al. |
| 4,113,173 A | 9/1978 | Lolachi |
| 4,146,172 A | 3/1979 | Cullis et al. |
| 4,151,844 A | 5/1979 | Cullis et al. |
| 4,187,979 A | 2/1980 | Cullis et al. |
| 4,198,972 A | 4/1980 | Herb |
| 4,241,866 A | 12/1980 | Giesbert et al. |
| 4,256,120 A | 3/1981 | Finley |
| 4,268,393 A | 5/1981 | Persidsky et al. |
| 4,269,718 A | 5/1981 | Persidsky |
| 4,303,193 A | 12/1981 | Latham, Jr. |
| 4,316,576 A | 2/1982 | Cullis et al. |
| 4,322,298 A | 3/1982 | Persidsky |
| 4,350,283 A | 9/1982 | Leonian |
| 4,356,958 A | 11/1982 | Kolobow et al. |
| 4,370,983 A | 2/1983 | Lichtenstein |
| 4,386,730 A | 6/1983 | Mulzet |
| 4,413,771 A | 11/1983 | Rohde et al. |
| 4,413,772 A | 11/1983 | Rohde et al. |
| 4,416,654 A | 11/1983 | Schoendorfer et al. |
| 4,419,089 A | 12/1983 | Kolobow et al. |
| 4,421,503 A | 12/1983 | Latham, Jr. et al. |
| 4,425,112 A | 1/1984 | Ito |
| 4,430,072 A | 2/1984 | Kellogg et al. |
| 4,443,345 A | 4/1984 | Wells |
| 4,447,220 A | 5/1984 | Eberle |
| 4,447,221 A | 5/1984 | Mulzet |
| 4,464,167 A | 8/1984 | Schoendorfer et al. |
| 4,493,691 A | 1/1985 | Calari |
| 4,557,719 A | 12/1985 | Neumann et al. |
| 4,610,846 A | 9/1986 | Martin |
| 4,647,279 A | 3/1987 | Mulzet et al. |
| 4,663,296 A | 5/1987 | Revillet et al. |
| 4,670,002 A | 6/1987 | Koreeda et al. |
| 4,671,102 A | 6/1987 | Vinegar et al. |
| 4,675,117 A | 6/1987 | Neumann et al. |
| 4,680,025 A | 7/1987 | Kruger et al. |
| 4,701,267 A | 10/1987 | Watanabe et al. |
| 4,708,710 A | 11/1987 | Dunn, Jr. |
| 4,708,712 A | 11/1987 | Mulzet |
| 4,720,284 A | 1/1988 | McCarty |
| 4,724,317 A | 2/1988 | Brown et al. |
| 4,738,655 A | 4/1988 | Brimhall et al. |
| 4,792,372 A | 12/1988 | Alexander et al. |
| 4,798,579 A | 1/1989 | Penhasi |
| 4,808,151 A | 2/1989 | Dunn, Jr. et al. |
| 4,834,890 A | 5/1989 | Brown et al. |
| 4,846,974 A | 7/1989 | Kelley et al. |
| 4,850,952 A | 7/1989 | Figdor et al. |
| 4,851,126 A | 7/1989 | Schoendorfer |
| 4,885,137 A | 12/1989 | Lork |
| 4,911,833 A | 3/1990 | Schoendorfer et al. |
| 4,915,847 A | 4/1990 | Dillon et al. |
| 4,933,291 A | 6/1990 | Daiss et al. |
| 4,934,995 A | 6/1990 | Cullis |
| 4,936,820 A | 6/1990 | Dennehey et al. |
| 4,936,998 A | 6/1990 | Nishimura et al. |
| 4,939,081 A | 7/1990 | Figdor et al. |
| 4,939,087 A | 7/1990 | Van Wie et al. |
| 4,963,498 A | 10/1990 | Hillman et al. |
| 4,968,295 A | 11/1990 | Neumann |
| 4,990,132 A | 2/1991 | Unger et al. |
| 5,006,103 A | 4/1991 | Bacehowski et al. |
| 5,039,401 A | 8/1991 | Columbus et al. |
| 5,076,911 A | 12/1991 | Brown et al. |
| 5,078,671 A | 1/1992 | Dennehey et al. |
| 5,089,146 A | 2/1992 | Carmen et al. |
| 5,100,564 A | 3/1992 | Pall et al. |
| 5,104,526 A | 4/1992 | Brown et al. |
| 5,121,470 A | 6/1992 | Trautman |
| 5,160,310 A | 11/1992 | Yhland |
| 5,178,603 A | 1/1993 | Prince |
| 5,203,999 A | 4/1993 | Hugues |
| 5,213,970 A | 5/1993 | Lopez-Berestein et al. |
| 5,217,426 A | 6/1993 | Bacehowski et al. |
| 5,217,427 A | 6/1993 | Cullis |
| 5,224,921 A | 7/1993 | Dennehey et al. |
| 5,229,012 A | 7/1993 | Pall et al. |
| 5,260,598 A | 11/1993 | Brass et al. |
| 5,282,982 A | 2/1994 | Wells |
| 5,298,171 A | 3/1994 | Biesel |
| 5,316,666 A | 5/1994 | Brown et al. |
| 5,316,667 A | 5/1994 | Brown et al. |
| 5,321,800 A | 6/1994 | Lesser |
| 5,322,620 A | 6/1994 | Brown et al. |
| 5,360,542 A | 11/1994 | Williamson, IV et al. |
| 5,362,291 A | 11/1994 | Williamson, IV |
| 5,370,802 A | 12/1994 | Brown |
| 5,397,479 A | 3/1995 | Kass et al. |
| 5,405,308 A | 4/1995 | Headley et al. |
| 5,409,813 A | 4/1995 | Schwartz |
| 5,437,624 A | 8/1995 | Langley |
| 5,494,592 A | 2/1996 | Latham, Jr. et al. |
| 5,496,265 A | 3/1996 | Langley et al. |
| 5,501,795 A | 3/1996 | Pall et al. |
| 5,525,218 A | 6/1996 | Williamson, IV et al. |
| 5,529,691 A | 6/1996 | Brown |
| 5,547,591 A | 8/1996 | Hagihara et al. |
| 5,549,834 A | 8/1996 | Brown |
| 5,571,068 A | 11/1996 | Bacehowski et al. |
| 5,577,513 A | 11/1996 | Van Vlasselaer |
| 5,580,465 A | 12/1996 | Pall et al. |
| 5,581,687 A | 12/1996 | Lyle et al. |
| 5,587,070 A | 12/1996 | Pall et al. |
| 5,607,830 A | 3/1997 | Biesel et al. |
| 5,628,915 A | 5/1997 | Brown et al. |
| 5,641,414 A | 6/1997 | Brown |
| 5,653,887 A | 8/1997 | Wahl et al. |
| 5,656,163 A | 8/1997 | Brown |
| 5,674,173 A | 10/1997 | Hlavinka et al. |
| 5,690,835 A | 11/1997 | Brown |
| 5,702,357 A | 12/1997 | Bainbridge et al. |
| 5,704,888 A | 1/1998 | Hlavinka et al. |
| 5,704,889 A | 1/1998 | Hlavinka et al. |
| 5,720,716 A | 2/1998 | Blakeslee et al. |
| 5,722,926 A | 3/1998 | Hlavinka et al. |
| 5,792,038 A | 8/1998 | Hlavinka |
| 5,792,372 A | 8/1998 | Brown et al. |
| 5,858,251 A | 1/1999 | Borchardt et al. |
| 5,904,645 A | 5/1999 | Hlavinka |
| 5,906,570 A | 5/1999 | Langley et al. |
| 5,913,768 A | 6/1999 | Langley et al. |
| 5,939,319 A | 8/1999 | Hlavinka et al. |
| 5,948,271 A | 9/1999 | Wardwell et al. |
| 5,951,877 A | 9/1999 | Langley et al. |
| 5,954,626 A | 9/1999 | Hlavinka |
| 6,011,490 A | 1/2000 | Tonnesen et al. |

(56) References Cited

U.S. PATENT DOCUMENTS

| | | | |
|---|---|---|---|
| 6,022,306 | A | 2/2000 | Dumont et al. |
| 6,053,856 | A | 4/2000 | Hlavinka |
| 6,071,422 | A | 6/2000 | Hlavinka et al. |
| 6,168,561 | B1 | 1/2001 | Cantu et al. |
| 6,325,750 | B1 | 12/2001 | Jorgensen et al. |
| 6,334,842 | B1 | 1/2002 | Hlavinka et al. |
| 6,338,820 | B1 | 1/2002 | Hubbard et al. |
| 6,352,499 | B1 | 3/2002 | Geigle |
| 6,354,986 | B1 | 3/2002 | Hlavinka et al. |
| 6,413,200 | B1 | 7/2002 | Jorgensen et al. |
| 6,495,351 | B2 | 12/2002 | McHale |
| 6,514,189 | B1 | 2/2003 | Hlavinka et al. |
| 6,574,173 | B1 | 6/2003 | Manes |
| 6,632,399 | B1 | 10/2003 | Kellogg et al. |
| 6,723,238 | B2 | 4/2004 | Romanauskas et al. |
| 6,790,371 | B2 | 9/2004 | Dolecek |
| 6,802,804 | B1 | 10/2004 | Stroucken |
| 7,029,430 | B2 | 4/2006 | Hlavinka et al. |
| 7,033,512 | B2 | 4/2006 | Hlavinka et al. |
| 7,201,848 | B2 | 4/2007 | Antwiler et al. |
| 7,422,693 | B2 | 9/2008 | Carter et al. |
| 7,531,098 | B2 * | 5/2009 | Robinson et al. ............ 210/787 |
| 7,549,956 | B2 | 6/2009 | Hlavinka et al. |
| 7,582,049 | B2 | 9/2009 | Hlavinka et al. |
| 7,588,692 | B2 | 9/2009 | Antwiler et al. |
| 7,605,388 | B2 | 10/2009 | Carter et al. |
| 7,857,744 | B2 | 12/2010 | Langley et al. |
| 7,963,901 | B2 * | 6/2011 | Langley et al. ................. 494/45 |
| 8,226,537 | B2 * | 7/2012 | Pittinger et al. ............... 494/45 |
| 2004/0104182 | A1 * | 6/2004 | Holmes et al. ............... 210/787 |
| 2006/0147895 | A1 | 7/2006 | Purdum |
| 2007/0102374 | A1 | 5/2007 | Kolenbrander |
| 2012/0316049 | A1 * | 12/2012 | Holmes et al. .................... 494/2 |

FOREIGN PATENT DOCUMENTS

| | | | |
|---|---|---|---|
| DE | 3700122 | A1 | 7/1988 |
| EP | 0057907 | B1 | 12/1986 |
| EP | 0392475 | A2 | 10/1990 |
| EP | 0406485 | A1 | 1/1991 |
| EP | 0363120 | B1 | 11/1993 |
| EP | 0284764 | B1 | 5/1994 |
| EP | 0419346 | B1 | 1/1995 |
| EP | 0408462 | B1 | 6/1995 |
| EP | 0729790 | B1 | 1/1996 |
| WO | 87/06857 | A1 | 11/1987 |
| WO | 89/02273 | A1 | 3/1989 |
| WO | 92/00145 | A1 | 1/1992 |
| WO | 94/02157 | A1 | 2/1994 |
| WO | 94/27698 | A2 | 12/1994 |
| WO | 95/03107 | A1 | 2/1995 |
| WO | 96/39618 | A1 | 12/1996 |
| WO | 96/40402 | A1 | 12/1996 |
| WO | 97/30748 | A1 | 8/1997 |
| WO | 01/97943 | A1 | 12/2001 |

OTHER PUBLICATIONS

Angelbeck, Judy H., "Adverse Reactions to Platelet Transfusion, Risks and Probably Causes", 1994, pp. 1-14, Pall Corporation.
Baxter Helathcare Corporation, Fenwal Division, "CS-3000 Plus Blood Cell Separator Operator's Manual", undated.
Beckman, "Centrifugal Elutriation", (undated), Beckman Instruments, Inc.
Besso, Nancy and Brandwein, Harvey, "Asahi Sepacell PL-10A Leukocyte Removal Filter: Effect of Post-Filtration Flush With Saline", Pall Technical Report, 1991, Pall Biomedical Products Corporation.
Biofil, "Systems for Filtration of Haemocomponents", (undated), Biofil Biomedical Devices.
Brandwein, Harvey Ph.D. and Besso, Nancy M.T. (ASCP), "Asahi Sepacell PL-10A Leukocyte Removal Filter: Efficiency with Random Donor Platelet Pools", Pall Technical Report, 1991, Pall Biomedical Products Corporation.
Brown, R. et al., "Evaluation of a New Separation Method Utilizing Plasma Recirculation and Autoelutriation", Transfusion, 1994, Supplement, vol. 34.
Bruil, A. et al., "Asymmetric Membrane Filters for the Removal of Leukocytes from Blood", Journal of Biomedical Materials Research, 1991, pp. 1459-1480, vol. 25, John Wiley & Sons, Inc.
Buchanan, A.S. and Heymann E., "Principle of a Counter-streaming Centrifuge for the Separation of Particles of Different Sizes", Nature, Apr. 24, 1948, pp. 648-649.
Burgstaler, E.A.; Pineda, A.A and Harbaugh, C.A., "White Blood Cell Contamination of Apheresis Platelets Collected on the COBE Spectra", COBE Blood Component, Technology, 1992, COBE Laboratories, Inc.
COBE BCT, Inc., "Cobe Spectra Apheresis System—Operator's Manual, Section 1", 1991, Lakewood, Colorado.
Drumheller, P.D. et al., "The Effects of RPM and Recycle on Separation Efficiency in a Clinical Blood Cell Centrifuge", Journal of Biomechanical Engineering, Nov. 1987, pp. 324-329, vol. 109.
Dzik, Sunny, "Leukodepletion Blood Filters: Filter Design and Mechanisms of Leukocyte Removal," Transfusion Medicine Reviews, Apr. 1993, pp. 65-77, vol. VII, No. 2, W.B. Saunders Company.
Faradji, A. et al., "Large Scale Isolation of Human Blood Monocytes by Continuous Flow Centrifugation Leukapheresis and Counterflow Centrifugation Elutriation for Adoptive Cellular Immunotherapy in Cancer Patients", Journal of Immunological Methods, 1994, pp. 297-309, vol. 174, Elsevier Science B.V.
Figdor, Carl G. et al., "Isolation of Functionally Different Human Monocytes by Counterilow Centrifugation Elutriation", Blood, Jul. 1982, pp. 46-53, vol. 60, No. 1, Grune & Stratton, Inc.
Figdor, Carl G. et al., "Theory and Practice of Centrifugal Elutriation (CE): Factors Influencing the Separation of Human Blood Cells", Cell Biophysics, 1983, pp. 105-118, vol. 5, Humana Press Inc.
Freedman, J. et al., "White Cell Depletion of Red Cell and Pooled Random-Donor Platelet Concentrates by Filtration and Residual Lymphocyte Subset Analysis", Transfusion, 1991, pp. 433-440, vol. 31, No. 5.
Gao, Ino K. et al., "Implementation of a Semiclosed Large Scale Counterflow Centrifugal Elutriation System", Journal of Clinical Apheresis, 1987, pp. 154-160 vol. 3, Alan R. Liss, Inc.
Grabske, Robert J., "Separating Cell Populations by Elutriation", (undated).
Griffith, Owen M., "Separation of T and B Cells from Human Peripheral Blood by Centrifugal Elutriation", Analytical Biochemistry, 1978, pp. 97-107, vol. 87.
Haemonetics, "Haemonetics Mobile Collection System Owner's Operating and Maintenance Manual", 1991, Haemonetics Corporation.
Heddle, N.M. et al., "A Prospective Study to Identify the Risk Factors Associated with Acute Reactions to Platelet and Red Cell Transfusions", Transfusion, 1993, pp. 794-797, vol. 33.
Heddle, Nancy M. et al., "The Role of the Plasma from Platelet Concentrates in Transfusion Reactions", The New England Journal of Medicine, Sep. 8, 1994, pp. 625-628 and 670-671, vol. 331, No. 10, Massachusetts Medical Society.
Hogman, Claes F., "Leucocyte Depletion of Blood Components—Present Trends and the Future. An Introduction", Leucocyte Depletion of Blood Components, 1994, pp. 1-4, VU University Press.
International Search Report and Written Opinion, PCT/US2012/042080, Nov. 7, 2012.
International Search Report and Written Opinion, PCT/US2014/016248, Jun. 3, 2014.
International Search Report, PCT/US03/11624, Aug. 4, 2003.
International Search Report, PCT/US2004/021344, Nov. 17, 2004.
Jemionek, John F. and Monroy, Rodney L., "Special Techniques for the Separation of Hemopoietic Cells", Current Methodology in Experimental Hematology, 1984, pp. 12-41, No. 48, Karger.
Kauffman, Michael G. et al., "Isolation of cell Cycle Fractions by Counterflow Centrifugal Elutriation", Analytical Biochemistry, 1990, pp. 41-46, vol. 191, Academic Press, Inc.
Keng, P.C.; Li C.K.N. and Wheeler K.T., "Characterization of the Separation Properties of the Beckman Elutriator System", Cell Biophysics, 1981, pp. 41-56, vol. 3, The Humana Press, Inc.

(56) References Cited

OTHER PUBLICATIONS

Lindahl, P.E., "On Counter Streaming Centrifugation in the Separation of Cells and Cell Fragments", Biochemica Et BioPhysica Acta, 1956, pp. 411-415, vol. 21.

Oxford, R.J. et al., "Interface Dynamics in a Centrifugal Cell Separator", Transfusion, 1988, pp. 588-592, vol. 28, No. 6.

Oxford, R.J. et al., "Monitoring and Automated Optimization of a Cell Centrifuge", IEEE/Eighth Annual Conference of the Engineering in Medicine and Biology Society, 1986, pp. 925-927, IEEE.

Pall Biomedical Products Company, "Benefits of Leukocyte Filtration for Red Cell and Platelet Blood Products", Tranfusion Associated CMV, 1994, Pall Corporation.

Pall Biomedical Products Company, "Lower is Better", 1994.

Persidsky, Maxim D. and Ling, Nan-Sing, "Separation of Platelet-Rich Plasma by Modified Centrifugal Elutriation", Journal of Clinical Apheresis, 1982, pp. 18-24, vol. 1.

Plas, Aart et al., "A New Multichamber Counterflow Centrifugation Rotor with High-separation Capacity and Versatile Potentials", Experimental Hematology, 1988, pp. 355-359, vol. 16, International Society for Experimental Hematology.

Price, T.H.; Northway, M.M and Moore, R.C., "Platelet Collection Using the COBE Spectra", COBE Blood Component Technology, 1989, COBE Laboratories, Inc.

Salgaller, Michael L., "A Manifesto on the Current State of Dendritic Cells in Adoptive Immunotherapy", Transfusion, Apr. 2003, pp. 422-424, vol. 43.

Sanderson, Richard J. et al., "Design Principles for a Counterflow Centrifugation Cell Separation Chamber", Analytical Biochemistry, 1976, pp. 615-622, vol. 71.

Sanderson, Richard J., "Separation of Different Kinds of Nucleated Cells from Blood by Centrifugal Elutriation", Cell Separation: Methods and Selected Applications, 1982, pp. 153-168, vol. 1, Academic Press, Inc.

Sniecinski, I., "Prevention of Immunologic and Infectious Complications of Transfusion by Leukocyte Depletion", (undated), pp. 202-211.

Stack, G. and Snyder, E.L., "Cytokine Generation in Stored Platelet Concentrates", Transfusion, 1994, pp. 20-25, vol. 34, No. 1.

Takahashi, T.A. et al., "Bradykinin Formation in a Platelet Concentrated Filtered With a Leukocyte-removal Filter Made of Nonwoven Polyester Fibers With a Negatively Charged Surface" (undated).

Tulp, A. and Barnhoorn, M.G., "A Separation Chamber to Sort Cells and Cell Organelles by Weak Physical Forces, V. A Sector-Shaped Chamber and Its Application to the Separation of Peripheral Blood Cells", Journal of Immunological Methods, 1984, pp. 281-295, vol. 69, Elsevier Science Publishers B.V.

Van Wie, Bernard J. Ph.D. and Hustvedt, Eric L. M.S., "The Effect of Hematocrit and Recycle on Cell Separations", Plasma Therapy Transfusion Technology, 1986, pp. 373-388, vol. 7, No. 3.

Van Wie, Bernard John, "Conceptualization and Evaluation of Techniques for Centrifugal Separation of Blood Cells: Optimum Process Conditions, Recycle, and Stagewise Processing", Dissertation, 1982, pp. 27-58.

Whitbread, J. Ph.D. et al., "Performance Evaluation of the Sepacell PL10A Filter and Pall PXL8 Filter: Measurement of Leukocyte Residuals and Consistency", Pall Technical Report, (undated), Pall Biomedical Products Company.

* cited by examiner

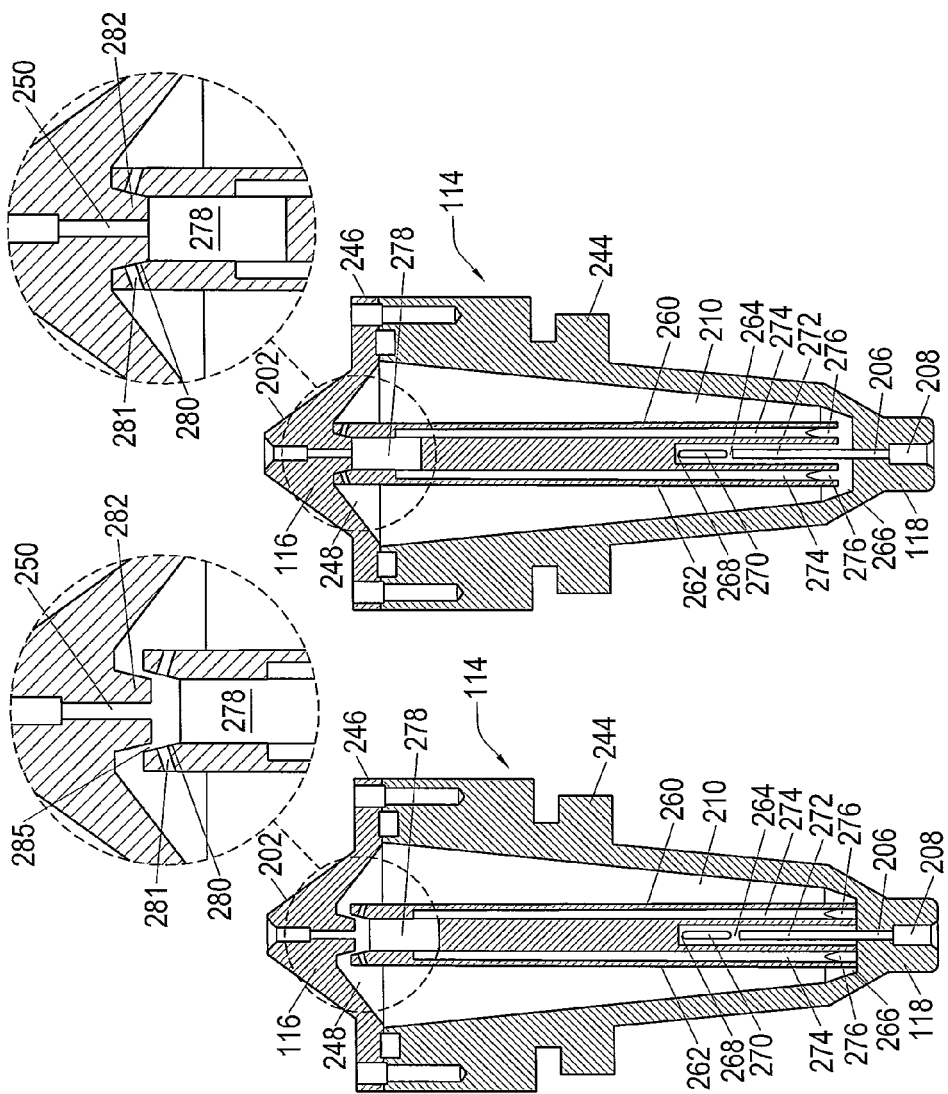
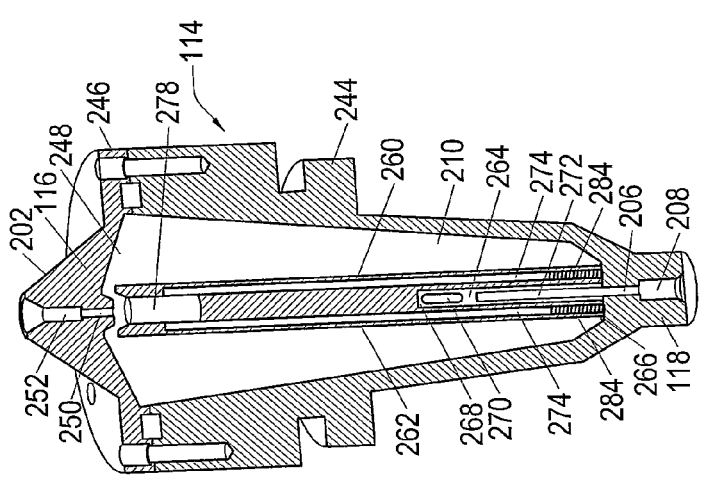

SYSTEM FOR BLOOD SEPARATION WITH A SEPARATION CHAMBER HAVING AN INTERNAL GRAVITY VALVE

CROSS-REFERENCE TO RELATED PATENT APPLICATIONS

This patent application claims priority to U.S. Provisional Patent Application No. 61/765,948, filed on Feb. 18, 2013, and hereby incorporated by references in its entirety as if set forth herein in full.

BACKGROUND OF INVENTION

Blood collection and blood processing play important roles in the worldwide health care system. In conventional large scale blood collection, blood is removed from a donor or patient, separated into its various blood components via centrifugation, filtration, or elutriation and stored in sterile containers for future infusion into a patient for therapeutic use. The separated blood components typically include fractions comprising red blood cells, white blood cells, platelets, and plasma. Separation of blood into its components can be performed continuously during collection ("apheresis") or can be performed subsequent to collection in batches, particularly with respect to the processing of whole blood samples. Separation of blood into its various components under highly sterile conditions is critical to many therapeutic applications.

Recently, apheresis blood collection techniques have been adopted in many large scale blood collection centers wherein a selected component of blood is collected and the balance of the blood is returned to the donor during collection. In apheresis, blood is removed from a donor and immediately separated into its components by on-line blood processing methods. Typically, on-line blood processing is provided by density centrifugation, filtration, or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation.

Both conventional blood collection and apheresis systems typically employ differential centrifugation methods for separating blood into its various blood components. In differential centrifugation, blood is circulated through a sterile blood processing vessel which is rotated at high rotational speeds about a central rotation axis. Rotation of the blood processing vessel creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887 and U.S. Pat. No. 7,033,512.

To achieve continuous, high throughput blood separation, extraction or collect ports are provided in most blood processing vessels. Extraction ports are capable of withdrawing material from the separation chamber at adjustable flow rates and, typically, are disposed at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase. For example, if the fraction containing white blood cells resides too close to the extraction port corresponding to platelet enriched plasma, white blood cells may enter the platelet enriched plasma stream exiting the blood processing vessel, thereby degrading the extent of separation achieved during blood processing. Although conventional blood processing via density centrifugation is capable of efficient separation of individual blood components, the purities of individual components obtained using this method is often not optimal for use in many therapeutic applications.

As a result of the inability to achieve optimal purity levels using centrifugation separation alone, a number of complementary separation techniques based on filtration, elutriation in a cell separation chamber and affinity-based techniques have been developed to achieve the optimal purities needed for use of blood components as therapeutic agents. These techniques, however, often reduce the overall yield realized and may reduce the therapeutic efficacy of the blood components collected. Exemplary methods and devices of blood processing via filtration, elutriation and affinity based methods are described in U.S. Pat. No. 6,334,842.

A centrifugal blood component separation apparatus has been described in commonly assigned U.S. Pat. No. 7,605,388, for instance. As described in U.S. Pat. No. 7,605,388, an optical cell may be configured such that white blood cells can be extracted through a first extraction port, plasma and/or platelets can be extracted through second extraction port, and red blood cells can be extracted through third extraction port. As also mentioned in U.S. Pat. No. 7,605,388 (but not shown), optical cells of a blood separation vessel can include one or more dams positioned proximate to the extraction ports to facilitate selective extraction of separated blood components having reduced impurities arising from adjacent components. The use of dams in blood processing via density centrifugation is known in the art and described in U.S. Pat. Nos. 6,053,856; 6,334,842 and 6,514,189.

Commonly assigned U.S. patent application Ser. No. 13/494,770 discloses an apparatus that controls flow selection between the top of the separation chamber and the bottom of the separation chamber by a valve, that is responsive to centrifugal force, hereinafter a "gravity" valve. The gravity valve is mounted on a rotor of a centrifugal blood separation device. When the rotor spins at high speed, thereby producing a high gravity field, the gravity valve may open a first flow path and may close a second flow path. When the rotor spins at a lower speed, the gravity valve may open the second flow path and close the first flow path. The flow paths may comprise tubular lines of flexible polymer. The gravity valve allows a line to be closed or opened dependant on the speed of rotation of the rotor without requiring electrical connections between the generally stationary blood separation device and the spinning rotor. Moreover, cells may be withdrawn from the bottom of the separation chamber through the second flow path with only a small amount of additional fluid, or "flush volume", added to the separation chamber.

The disclosed gravity valve of U.S. application Ser. No. 13/494,770 is mounted on the rotor or "filler", that is, on the spinning part of a centrifuge that holds the disposable separation chamber. The remains a need for a disposable blood separation set that can be mounted on a centrifuge wherein the disposable blood separation set comprises a separation chamber having an integral gravity valve. The gravity valve being integral with the separation chamber, the apparatus would not require a specialized rotor or filler.

SUMMARY OF THE INVENTION

This invention provides methods, devices and device components for improving the processing of fluids comprising fluid components, such as blood, components of blood and fluids derived from blood. Methods, devices and device components of the present invention are capable of monitoring and controlling separation of blood into discrete components and subsequent collection of selected components. In particular, it has been found that white blood cells may be extracted from the bottom of a fluidized bed leuko-reduction chamber (or cell separation chamber) while plasma and platelets are removed from the top of the separation chamber. The system and method may enable collection of white blood cells with fewer platelets.

A function of the centrifuge blood processing system described herein may be the collection of white blood cells or other selected blood components such as mesenchymal stem cells. In a preferred embodiment, certain functions of the centrifugal blood separator are controlled by an optical monitoring system. A cell separation chamber, adapted to be mounted on a rotor of the centrifuge blood processing system, comprises an inlet for receiving plasma, platelets and white blood cells, or "buffy coat", and an outlet for ejecting plasma and platelets from the separation chamber. Red blood cells or plasma may be collected or returned to a donor. White cells or other components such as mesenchymal stem cells and plasma may be collected for therapeutic purposes.

According to an embodiment, an optical cell of a circumferential blood processing vessel comprises at least a buffy coat extraction port and a red blood cell extraction port. White cells collect at the buffy coat extraction port. This configuration allows white cell-containing buffy coat to be withdrawn from the blood processing vessel through the buffy coat extraction port for further separation in the fluidized-bed filtration chamber or cell separation chamber. The cell separation chamber has a generally conical shape, with a buffy coat inlet at the apex of the cone and adapted to be mounted with the buffy coat inlet radially outwardly on the centrifuge rotor. A plasma outlet is centrally located in the base of the cone and is adapted to be mounted radially inwardly on the centrifuge rotor. The base may also have a slight conical shape to conduct platelets and plasma to the plasma outlet. The inlet may comprise a pipe or tube extending into the interior of the separation chamber such that a circumferential well is formed between the pipe and an interior conical wall of the separation chamber. White blood cells ("WBC") fall into the well and white blood cells and plasma are withdrawn from the separation chamber through a distal end of a pipe for collection.

Features of the disclosed apparatus and method may reduce the loss of white blood cell product or selected cell components such as mesenchymal stem cells that can occur during periodic flushing of white blood cells through the platelet outlet, as in conventional separation chamber.

Further features may provide more continuous steady flow through a cell separation chamber, thereby providing a greater volume of blood components processed per unit time. Other features may produce a collected white blood cell (or other selected cell types) product having fewer platelets than conventional collection methods, and thus improved purity.

Yet other features of the disclosed apparatus and method may reduce collection flow rates out of the separation chamber and to reduce the volume of WBC-containing fluid extracted from the separation chamber. A low WBC extraction volume may be achieved with a cycled extraction rate that may be triggered by detection of a saturated separation chamber by the optical sensor. Total flow through the separation chamber may be kept constant.

A cell separation chamber for cell collection, as disclosed herein, may not be limited by insufficient available plasma for flushing the selected cells through the platelet outlet, as in a conventional separation chamber.

For donors whose blood has a high hematocrit, it has sometimes been difficult or impossible to reduce the RPM of the centrifuge rotor (and thereby reduce the gravitational field of the centrifuge) sufficiently to allow complete flushing of WBC out of the platelet outlet of a conventional separation chamber. The disclosed apparatus may not require a similar reduction in the centrifuge gravitational field when white blood cells are removed from the separation chamber.

These and other features and advantages will be apparent from the following description, drawings and claims.

BRIEF DESCRIPTION OF THE DRAWINGS

FIG. 5 is a cross-sectional view of a first embodiment of the cell separation chamber of FIG. 4.

FIG. 6 is a further cross-sectional view of the embodiment of FIG. 5.

FIG. 7 is an additional cross-sectional view of the embodiment according to FIG. 5.

DETAILED DESCRIPTION

To describe the present invention, reference will now be made to the accompanying drawings. The present invention may be used with a blood processing apparatus such as a SPECTRA OPTIA® blood component centrifuge manufactured by Terumo BCT, Inc. (formerly known as CaridianBCT, Inc.) or a TRIMA® or TRIMA ACCEL® blood component centrifuge also manufactured by Terumo BCT, Inc. (formerly known as CaridianBCT, Inc.) The invention may also be used with other blood component centrifuges. The above-named centrifuges incorporate a one-omega/two-omega seal-less tubing connection as disclosed in U.S. Pat. No. 4,425,112 to provide a continuous flow of blood to and from the rotor of an operating centrifuge without requiring a rotating seal.

An embodiment of the invention comprises an improved leuko-reduction or cell separation chamber for removal of white blood cells ("WBC") or other selected types of cells such as mesenchymal stem cells from blood components. A related separation chamber is described in commonly-assigned U.S. application Ser. No. 12/209,793.

It is desirable for a separation chamber to separate greater than 99.99% of entrained WBC from platelet or plasma products obtained by centrifugal apheresis, which is an extremely high value. The process for this separation is based on the phenomenon of particle sedimentation in a fluid. The separated WBC consist of about 95% mononuclear cells (which are about 90% leukocytes and 10% monocytes) and about 5% granulocytes. To accommodate the apheresis collection process, the separation chamber may function in an automatic mode as a continuous-feed process. This requires an overflowing saturated bed of platelets above a bed of mononuclear cells, which continuously accumulate during the collection. The saturated bed requirement operates in the dense-phase flow regime, which is characterized by high cell density. After a quantity or bolus of white blood cells are collected in the separation chamber, the WBC are removed from the chamber for collection. In devices with conventional separation chambers, this may be accomplished by reducing the rotational speed of the centrifuge and increasing the flow rate of plasma through the separation chamber, thus pushing the WBC bolus out of the outlet port.

In the disclosed embodiments, an internal gravity valve selectively allows flow through a first flow path near the inlet of the separation chamber and, alternatively, through a second flow path near the outlet of the separation chamber. The gravity valve responds to the speed of the centrifuge rotor, on which the valve is mounted, to close or open the paths. No additional electrical connection is needed to operate the valve.

Figure 1:
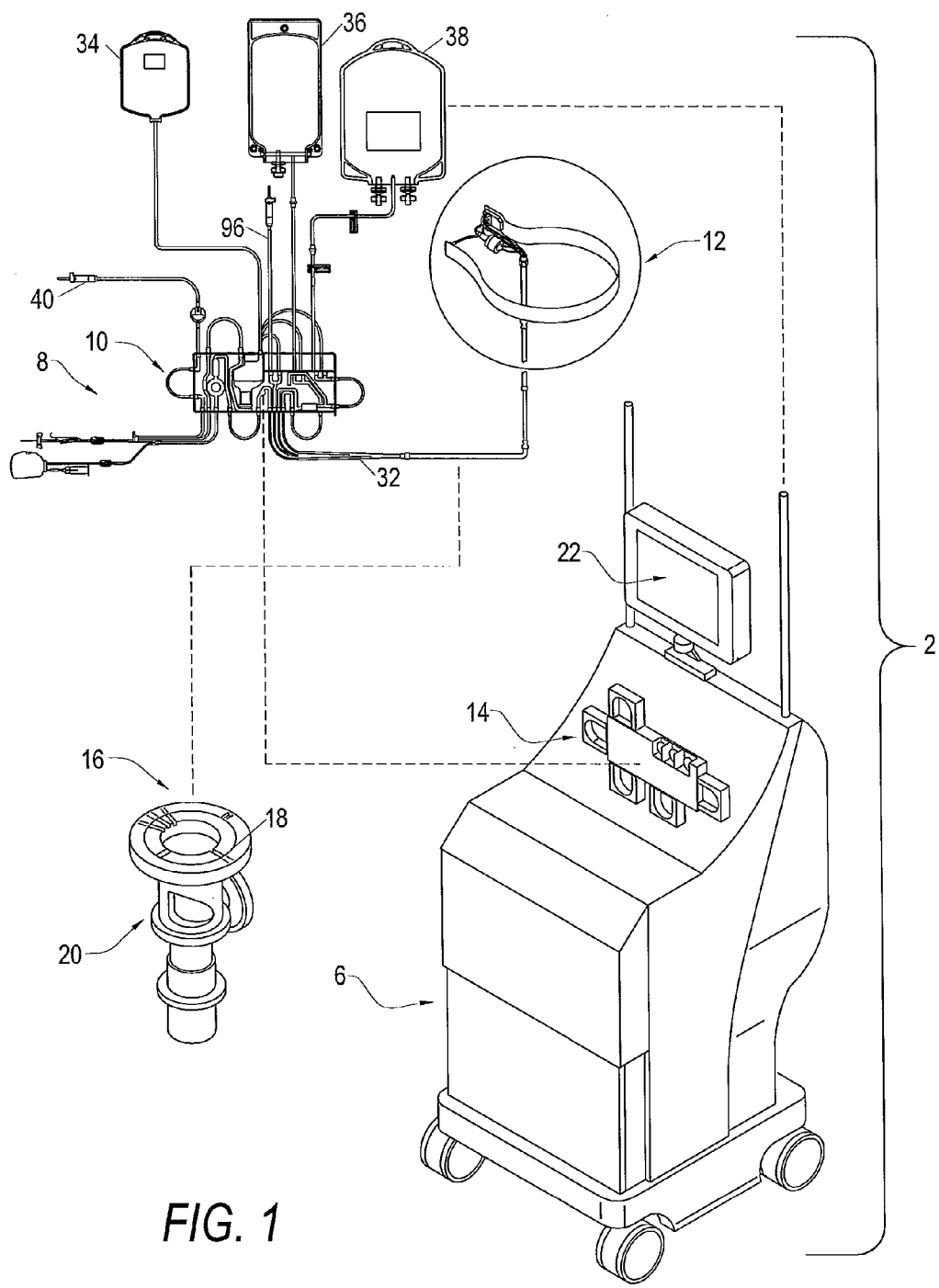
FIG. 1 is a schematic view of one embodiment of an apheresis system, which can be used in or with the present invention.

A blood apheresis system 2 is schematically illustrated in FIG. 1. System 2 provides for a continuous blood component separation process. Generally, whole blood is withdrawn from a donor and is provided to a blood component separation device 6 where the blood is separated into various components and at least one of these blood components is collected from the device 6. One or more of the separated blood components may be either collected for subsequent use or returned to the donor. In the blood apheresis system 2, blood is withdrawn from the donor and directed through a bag and tubing set 8, which includes an extracorporeal tubing circuit 10 and a blood processing vessel 12, which together define a closed, sterile, disposable system. The set 8 is adapted to be mounted in the blood component separation device 6. The separation device 6 includes a pump/valve/sensor assembly 14, which interfaces with the extracorporeal tubing circuit 10, and a centrifuge assembly 16, which interfaces with the blood processing vessel 12.

The centrifuge assembly 16 may include a channel 18 in a rotatable rotor assembly 20, which rotor assembly provides the centrifugal forces (sometimes referred to as a "gravitational field") required to separate blood into its various blood component types by centrifugation. The blood processing vessel 12 may then be fitted within the channel 18. Blood can flow substantially continuously from the donor, through the extracorporeal tubing circuit 10, and into the rotating blood processing vessel 12. Within the blood processing vessel 12, blood may be separated into various blood component types and at least one of these blood component types (e.g., white blood cells, platelets, plasma, or red blood cells) may be removed from the blood processing vessel 12. Blood components that are not being retained for collection or for therapeutic treatment (e.g., platelets and/or plasma) are also removed from the blood processing vessel 12 and returned to the donor via the extracorporeal tubing circuit 10. Various alternative apheresis systems (not shown) may also be used, including batch processing systems (non-continuous inflow of whole blood and/or non-continuous outflow of separated blood components) or smaller scale batch or continuous RBC/plasma separation systems, whether or not blood components may be returned to the donor.

Operation of the blood component separation device 6 is controlled by one or more processors included therein, and may advantageously comprise a plurality of embedded computer processors to accommodate interface with PC user facilities (e.g., CD ROM, modem, audio, networking and other capabilities). In order to assist the operator of the apheresis system 2 with various aspects of its operation, the blood component separation device 6 includes a graphical interface 22 with an interactive touch screen.

Figure 2:
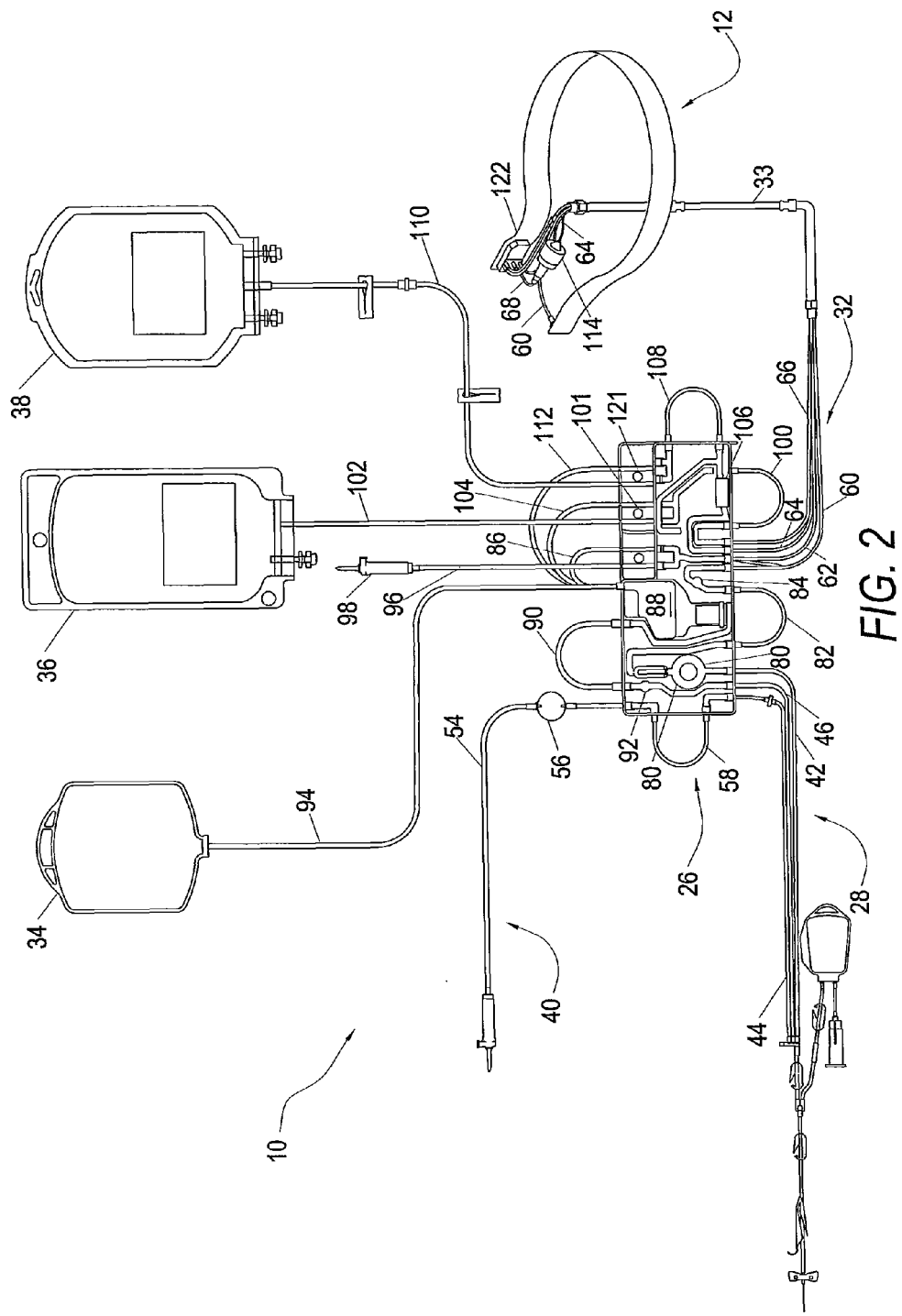
FIG. 2 illustrates a tubing and bag set including an extracorporeal tubing circuit, a cassette assembly, collection bag assembly, a blood processing vessel, and a cell separation chamber for use in or with the system of FIG. 1.

An extracorporeal tubing circuit 10, shown in FIG. 2, may include a cassette 26 and a number of tubing/collection assemblies 28, 32, 34, 36, 38 and 40. A blood removal-return tubing assembly 28 provides a needle interface for withdrawing blood from a donor to the remainder of the tubing circuit 10 and for returning blood components and other fluids to the donor. A single needle configuration is shown, but a double needle interface may also be used. Three lines 42, 44, 46 are provided in blood removal-return tubing assembly 28 for blood removal, blood return, and anti-coagulant. A cassette 26 is connected between the tubing assembly 28, which connects to the donor, and blood inlet/blood component tubing line sub-assembly 32, which provides the interface between cassette 26 and blood processing vessel 12. The cassette 26 orients tubing segments in predetermined spaced relationships within the cassette 26 for ultimate engagement with valve members on apheresis device 6. Such valves will, when activated, control flow through loops and tubing.

The tubing line sub-assembly 32 comprises four lines 60, 62, 64, and 66, shown in FIG. 2, for transport of blood and components to and from the processing vessel 12. The four lines are encased in a sheath 33 that allows the one omega-two omega motion described in U.S. Pat. No. 4,425,112. An anti-coagulant tubing assembly 40, a vent bag 34, a plasma collection assembly 36, and a white blood cell collection bag 38 are also interconnected with cassette 26. Optionally, a red blood cell collection assembly might also be provided through an auxiliary line 96, as is known in the art. The extracorporeal tubing circuit 10 and blood processing vessel 12 are pre-connected to form a closed, sterilized, disposable assembly for a single use.

When the tubing circuit 10 has been mounted on the blood component separation device 6, saline solution (not shown) primes the tubing circuit through a line 54 and filter 56 (see FIG. 2). Saline flows through an internal passageway in the cassette 26 and through the line 44 to the distal end of the blood removal assembly 28. Saline can then flow up a blood withdrawal line 42 into the other tubes and passageways of the circuit 10 in preparation for blood processing. A supply or bag (not shown) of anticoagulant can then be connected to a distal end of the anticoagulant tubing assembly 40 in place of a saline supply. Anticoagulant solution flows past the filter 56 and a first pump loop 58 through the anticoagulant line 44 to the distal end of the blood removal assembly. The pump loop 58 and other pump loops described herein couple with peristaltic pumps on the blood processing device 6 in a known manner. The device 6 controls the direction and rate of flow of the fluids described herein by controlling the speed and direction of the peristaltic pumps and the position of various valves.

The blood removal line 42 conducts blood into the cassette 26, where the blood passes a first pressure sensor 80 and a second pump loop 82. A second pressure sensor 84, between second pump loop 82 with its associated pump and blood inflow line 60 to the blood processing vessel 12, senses the fluid pressure effective at an inlet to the blood processing vessel 12. Emanating from blood processing vessel 12 is an RBC outlet tubing line 62 of the blood inlet/blood component tubing assembly 32. The outlet tubing line 62 connects to an external loop 86 to a return reservoir 88. The return reservoir 88 contacts sensors on the device 6 that detect low and high fluid levels. The device 6 keeps the fluid in the reservoir between these two levels by controlling flow out of the reservoir past a return pump loop 90 and a return pressure sensor 92. Because the fluid level in the reservoir 88 is constantly rising and falling, a vent bag 34 connects to the reservoir 88 through a vent tube 94. Air can flow between the reservoir 88 and the vent bag 34 in a sterile manner. Fluid flows into a return tube 46 in the blood removal-return assembly 28. The removal-return assembly 28 also comprises the line 44 for adding priming solution (saline) or anti-coagulant solution, as described above. If desired, red blood cells could be withdrawn through auxiliary line 96 and collected in a collection bag (not shown). Alternatively, a bag containing replacement fluid (not shown) may be connected to a spike or Luer connector 98 on the auxiliary line 96, allowing replacement fluid to pass through the return loop 86 into the reservoir 88. Blood components and replacement fluid are then returned to the donor. Equivalently, it is also known to couple the red blood cell line 62 to a peristaltic pump and to provide an automatic valve to select blood flow paths, as shown, for instance in U.S. patent application Ser. No. 12/959,987.

Plasma may also be collected from the blood processing vessel 12 into plasma bag 36. When desired, plasma is withdrawn from the blood processing vessel 12 through plasma line 66 to a pump loop 100. A valve 101 diverts the plasma either into a collect tube 102 to the plasma bag 36, or into connecting loop or line 104 to the reservoir 88. Excess plasma in the reservoir 88 is returned to the donor in the same way as red blood cells, as described above.

White blood cells and platelets flow out of the blood processing vessel 12 through a cell line 68 into a cell separation chamber 114, which is further described below. The contents of the separation chamber flow out of the separation chamber through an outlet line 64. The outlet line 64 passes through the tubing line sub-assembly 32 and sheath 33 to the cassette 26. In the cassette 26, the fluid from the outlet line passes a red-green photo sensor 106, which may be used to control periodic flushing of white blood cells out of the cell separation chamber 114 into the collect bag 38. The selected cells flow through a pump loop or line 108, which engages a peristaltic pump on the separation device 6. The pump loop 108 connects to a valved passageway in the cassette 26. The blood processing device 6 can control a valve 121 to direct white blood cells or other selected cells either into a collect tube 110 and thence into the collect bag 38, or into a connection loop or line 112 and thence into the reservoir 88. Excess white blood cells in the reservoir 88 may be returned to the donor in the same way as red blood cells and plasma, as described above.

During a blood removal, whole blood will be passed from a donor into tubing line 42 of blood removal tubing assembly 28. The blood is pumped by the device 6 via pump loop 82, to the blood processing vessel 12, via the cassette 26 and line 60 of the blood inlet/blood component tubing assembly 32. After separation processing in vessel 12, uncollected blood components are transferred from the processing vessel 12 to and through cassette 26 and into reservoir 88 of cassette 26, which is filled up to a predetermined level. The blood component separation device 6 may initiate a blood return submode wherein components may be returned to the donor through return line 46. The cycle between blood removal and blood return submodes will continue until a predetermined amount of blood components have been harvested. In an alternative double needle scheme, as is known in the art, blood may be removed from the donor and returned to a donor through two separate needles. See, for example, U.S. patent application Ser. No. 10/160,137.

A bracket (not shown) is provided on a top surface of the centrifuge assembly 16. The bracket releasably holds the cell separation chamber 114 on the centrifuge assembly 16 so that an outlet 116 of the cell separation chamber 114 is positioned closer to the axis of rotation than an inlet 118 of the chamber 114. The bracket orients the chamber 114 on the centrifuge assembly 16 with a longitudinal axis of the cell separation chamber 114 in a plane transverse to the rotor's axis of rotation. In addition, the bracket is arranged to hold the cell separation chamber 114 on the centrifuge assembly 16 with the cell separation chamber outlet 116 facing the axis of rotation. Although the chamber 114 is preferably on a top surface of the centrifuge assembly 16, the chamber 114 could also be secured to the centrifuge assembly 16 at alternate locations, such as beneath the top surface of the centrifuge assembly 16.

Figure 3:
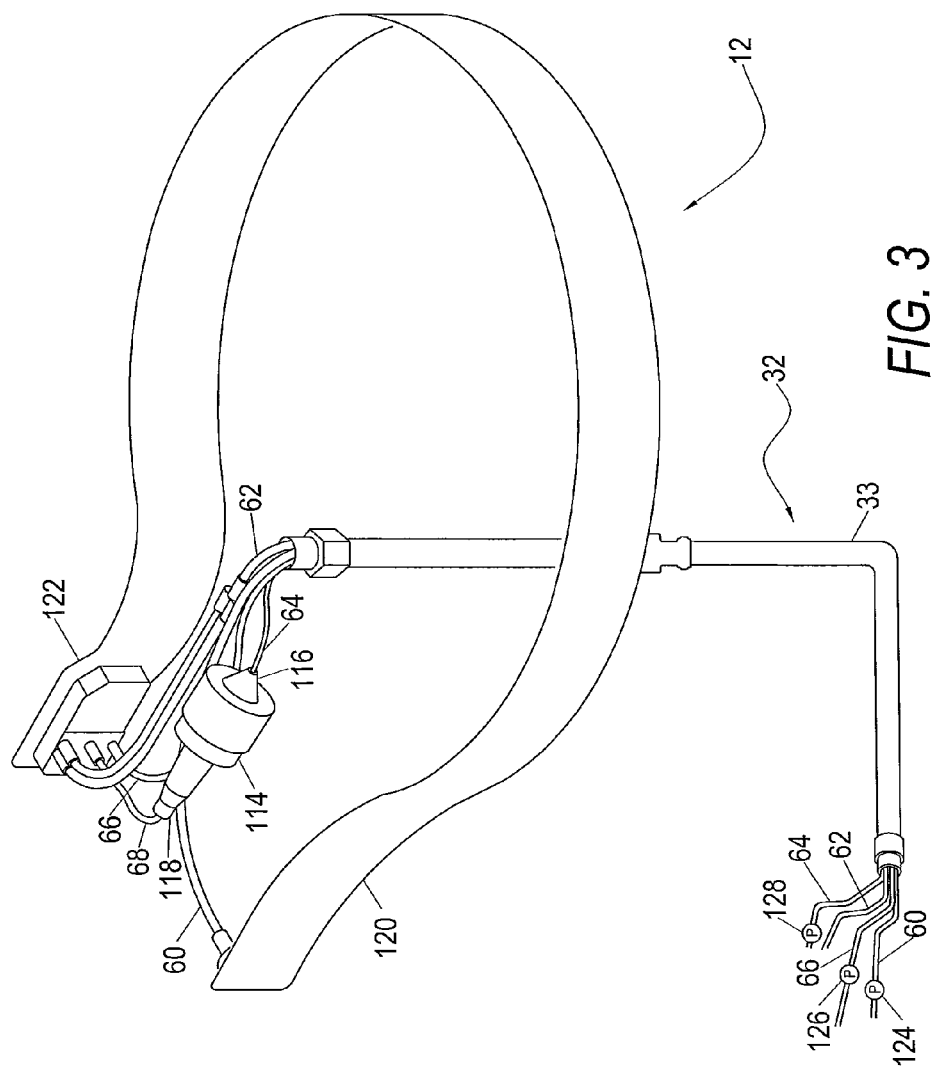
FIG. 3 is a perspective view of a blood processing vessel and the cell separation chamber.
Figure 4:
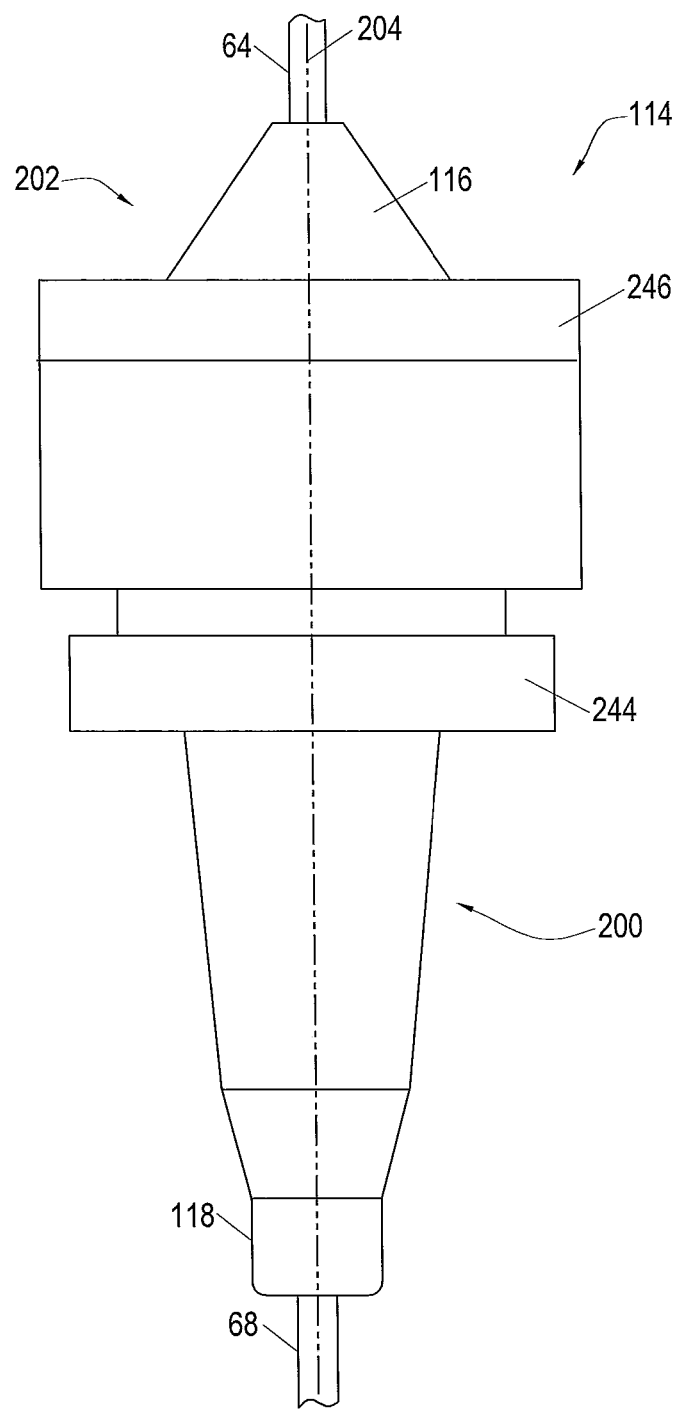
FIG. 4 is a plan view of the cell separation chamber of FIG. 3.

FIG. 3 schematically illustrates the blood processing vessel 12 and cell separation chamber 114. The blood processing vessel 12 has a generally annular flow path and includes an inlet portion 120 and an outlet portion 122. The inflow tube 60 connects to the inlet portion 120 for conveying a fluid to be separated, such as whole blood, into the blood processing vessel 12. During a separation procedure, substances entering the inlet portion 120 flow around the vessel 12 and stratify according to differences in density in response to rotation of the centrifuge assembly 16. The outlet portion 122 includes outlets for the RBC line 62, the plasma line 66, and buffy coat or white blood cell line 68 for removing separated substances from the blood processing vessel 12. Each of the components separated in the vessel 12 is collected and removed in only one area of the vessel 12, namely the outlet portion 122.

The outlet of the line 68 is connected to the cell separation chamber inlet 118 to pass intermediate density components, including white blood cells or mesenchymal stem cells (MNC), into the cell separation chamber 114. Components initially separated in the blood processing vessel 12 are further separated in the cell separation chamber 114. For example, white blood cells could be separated from plasma and platelets in the cell separation chamber 114. This further separation takes place by forming a saturated fluidized bed of particles in the cell separation chamber 114. Plasma and platelets would flow out of the cell separation chamber 114 while white blood cells were retained in the chamber. Similarly, granulocytes could be separated from red blood cells in like manner.

As schematically shown in FIG. 3, a plurality of pumps 124, 126, and 128 are provided for adding and removing substances to and from the blood processing vessel 12 and cell separation chamber 114. An inflow pump 124 is coupled to the inflow line 60 at pump loop 82 (FIG. 2) to supply the substance to be separated, such as whole blood, to the inlet portion 120. In addition, a first collection pump 126 is coupled at loop 100 to the plasma line 66. A second collection pump 128 is coupled to the collection line 64 at loop 108. The second collection pump 128 draws liquid and particles from the cell separation chamber outlet 116 and causes liquid and particles to enter the cell separation chamber 114 via the cell separation chamber inlet 118. In the disclosed embodiment, plasma and platelets are usually withdrawn from the outlet 116 of the cell separation chamber 114 through line 64. In the prior art, collected white blood cells or MNC or other components would be flushed from the chamber 114 through the cell collection line 64 by either increasing the fluid flow through the chamber 114 or by slowing the rotor or both. In the disclosed embodiments, on the other hand, an internal gravity valve selectively allows components to enter near the inlet or withdraw components near the inlet. Thus, the peristaltic pump 128, which is coupled to loop 108, can draw fluid either from the outlet 116 or near the inlet 118, depending on the internal gravity valve.

During the formation of the fluidized bed of cells in the chamber 114, platelet rich plasma (PRP) or platelets would ordinarily be drawn from the outlet 116 through line 64. During expression of collected cells (e.g., MNC), the collected cells would be drawn through the internal gravity valve from a location near the inlet 118, as explained below. Since the collected cells would be relatively heavier than plasma, they would tend to fall towards the inlet 118 and could more easily be withdrawn from the chamber 114. Beyond pump 128, loop 108 again divides into the two lines 110, 112. The valve 121 on the device 6 selectively opens and closes the lines. Line 112 is coupled to the reservoir 88 and ordinarily returns PRP to the donor. Line 110 is coupled to a collect bag 38 and allows the collected cells to flow into the collect bag 38.

The first collection pump 126, which is coupled to loop 100, removes primarily low-density substances such as plasma directly from the blood processing vessel 12 via the plasma line 66. The plasma could either be collected in plasma bag 36 through line 102, or returned to the donor through connecting loop or line 104 and the reservoir 88. Valve 101 selectively opens and closes the lines 102, 104 to direct the flow of plasma either to the bag 36 or to the reservoir 88.

The pumps 124, 126, and 128 are peristaltic pumps, which prevent significant damage to blood components. The pumps 124, 126, and 128 control the flow rate of substances flowing to and from the blood processing vessel 12 and the cell separation chamber 114. A saturated fluidized bed of particles is maintained within the cell separation chamber 114 to cause other particles to be retained in the cell separation chamber 114.

The cell separation chamber is shown in detail in FIGS. 4 through 10. FIGS. 5 through 7 and FIGS. 8 through 10 illustrate two embodiments of the present invention. Common to both embodiments, the cell separation chamber 114 may be constructed in two pieces, a main body 200 and a cap 202, both being symmetrical around an axis 204. The main body 200 has an inlet 118 comprising a through bore 206 and a concentric stopped bore 208. The diameter of the through bore 206 corresponds to the inside diameter of the cell line 68, while the diameter of the stopped bore 208 corresponds to the outside diameter of the line 68, so that the cell line 68 can be seated in the stopped bore 208 and a fluid passageway of constant diameter can be formed between the line 68 and the through bore 206. The through bore 206 opens into a frustro-conical segment 210.

In the illustrated embodiments, the main body 200 of the cell separation chamber 114 further comprises a circumferential flange 244, which is supported in the bracket. The cap 202 comprises a rim 246 that fits against the flange 244. An interlocking groove and ridge (not shown) may be provided between the rim 246 and flange 244 for sealing, if desired. The cap 202 and main body 200 may be joined by ultrasonic welding or other suitable techniques, such as machine screws, as shown. The cap opens into an abrupt frustro-conical segment 248. The abrupt segment 248 tapers towards the axis 204. The abrupt segment 248 funnels blood components into the outlet 116 without excessive turbulence or damage to the blood components. The outlet 116 comprises a through bore 250 and a concentric stopped bore 252. The diameter of the through bore 250 corresponds to the inside diameter of the outlet line 64, while the diameter of the stopped bore 252 corresponds to the outside diameter of the cell line 64, so that the line 64 can be seated in the stopped bore 252 and a fluid passageway of constant diameter can be formed between the line 64 and the through bore 250. The through bore 250 opens into the frustro-conical segment 248.

In the separation chamber 114, an overflowing saturated bed of platelets forms above a bed of mononuclear cells, which continuously accumulate during the collection process. The saturated bed operates in a dense-phase flow regime, which is characterized by high cell density. After a quantity or bolus of white blood cells or other selected cells is collected in the separation chamber, the cells are removed from the chamber for collection. The selected cells are drawn out of the separation chamber 114 from an area near the inlet 118, which is "down hill" with respect to the gravitational field created by the centrifuge apparatus. The speed of the centrifuge is only changed to operate the internal gravity valves, as explained below, and an increased inlet flow of plasma is not needed to flush the collected cells through the outlet 116.

A first embodiment of an internal gravity valve 260 is illustrated in FIGS. 5 through 7. The gravity valve 260 comprises a rod 262 symmetrically positioned around the axis 204 of the separation chamber 114. The rod has a density greater than the most dense fluid component to be separated in the separation chamber. Consequently, the rod 262 can be displaced from the outlet 116 to the inlet 118 of the chamber 114 by increasing the speed of the centrifuge, thereby increasing the gravitational field. As the chamber 114 is intended to be mounted on the rotor of the centrifuge with the outlet 116 closer to the axis of rotation of the rotor, the outlet end of the chamber will be referred to as "proximal" and the inlet end will be referred to as "distal" in this description.

The rod 262 has a centrally located distal bore 264, concentric with the axis 204, extending from a distal end 266 of the rod 262 about one third of the length of the rod. At a proximal stopped end 268 of the bore one or more vents 270 provide a fluid path into the frustro-conical segment 210 of the chamber 114. A pipe 272 extends from the through bore 206 of the inlet 118 to a location near the vents 270 in the rod, allowing fluid to flow from the inlet, through the pipe 272, out the vents 270 and into the frustro-conical segment, regardless of the position of the gravity valve 260.

The rod 262 also comprises one or more conduits 274 extending from the distal end to the proximal end of the rod 262 and positioned around the distal bore 264. The conduits 274 do not connect to the distal bore 264, but are in fluid connection with the interior of the separation chamber 114 through orifices 276 at the distal end of the rod and through a cavity 278 at the proximal end to the rod. As can be seen in the expanded views in FIGS. 6 and 7, the cavity 278 has a chamfered proximal edge 280 that mates with a male frustro-conical protrusion 282 surrounding the through bore 250 of the outlet 116. A plurality of holes 281 in the proximal edge 280 allow fluid, including particle, to flow from the interior of the separation chamber into the outlet 116 when the rod does not engage the protrusion 282. Springs 284, shown in FIG. 5, push the rod in the proximal direction, such that the rod is normally engaged with the protrusion 282, as shown in FIG. 7. The springs 284 are not shown in FIGS. 6 and 7 so that the orifices 276 can be shown.

During the process of separating a blood component such as platelets or white blood cells from plasma, for instance, the speed of the centrifuge allows the springs 284 to force the rod against the inlet 118 and away from the protrusion 282, as shown in FIGS. 5 and 6. The mixed components of the fluid leave the pipe 272 and enter the interior of the chamber 114 through the vents 270. A fluidized bed of selected, relatively heavier particles, such as white blood cells, accumulates in the chamber, while plasma and lighter particles, such as platelets, flow through a gap 285 between the chamfered edge 280 and the protrusion 282 and out the outlet 116. When a sufficient quantity of the heavier particles have accumulated in the chamber, the speed of the rotor is reduced and the springs 284 press the rod against the protrusion 282, as shown in FIG. 7. The gap 285 having been closed, the heavier particles are pushed into the orifices 276, through the conduits 274, into the cavity 278, and out the outlet 116. Additional fluid continues to enter the chamber through the vents 270 as the heavier particles are harvested from the distal end of the chamber. This allows the heavier particles to be collected more quickly, without excessive addition of new fluid.

Figure 8:
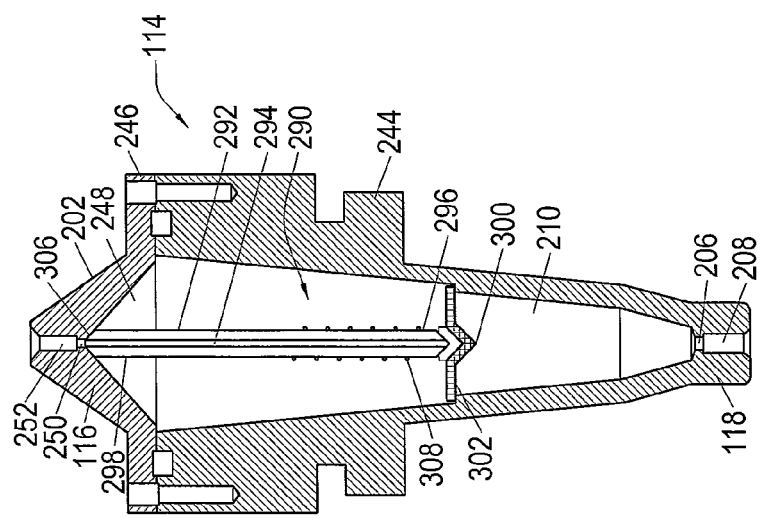
FIG. 8 is a perspective, cross-sectional view of a second embodiment of the cell separation chamber of FIG. 4.
Figure 9:
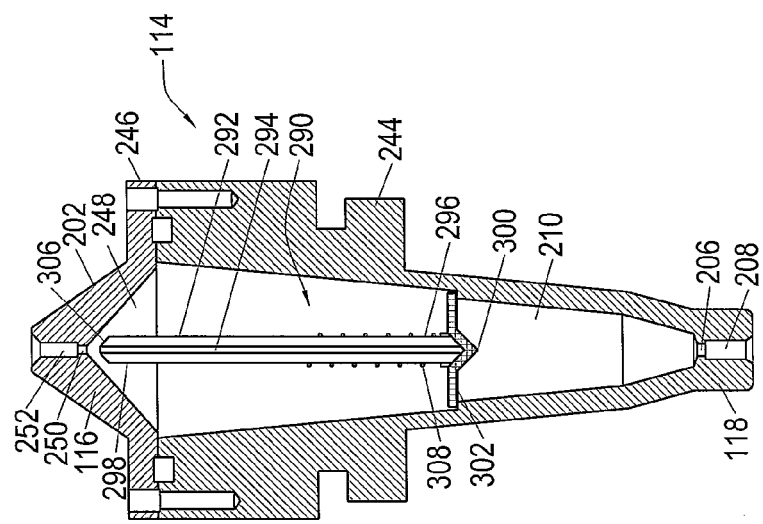
FIG. 9 is a plan, cross-sectional view of the embodiment of FIG. 8.
Figure 10:
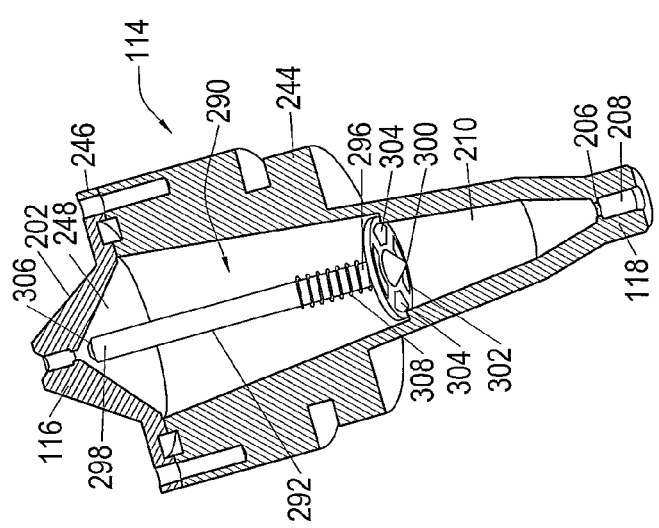
FIG. 10 is a second plan, cross-sectional view of the embodiment of FIG. 8.

The second embodiment of FIGS. 8 through 10 also features a second internal gravity valve 290 comprising a rod 292 having a lumen 294 extending from a distal end 296 to a proximal end 298 of the rod. The distal end 296 is chamfered 299 and engages a conical cup 300 in the center of a disc 302. The disc 302 is affixed to the frusto-conical segment 210 of the main body 200 of the separation chamber 114, about one-third of the distance from the inlet 118 to the outlet 116. The disc 302 has one or more openings 304 surrounding the central cup 300, which allow fluid to flow from the inlet 118 towards the outlet 116.

The proximal end 298 of the rod also has a chamfer 306 that engages the abrupt frustro-conical segment 248 adjacent the outlet 116. A spring 308 pushes the rod 292 against the outlet as shown in FIG. 10. During the separation phase, shown in FIG. 9, the speed of the centrifuge allows the spring 308 to force the rod against the cup 300 and away from the outlet 116, as shown in FIGS. 8 and 9. The mixed components of the fluid enter the interior of the chamber 114 at the inlet 118. As in the previously described embodiment, a fluidized bed of selected, relatively heavier particles, such as white blood cells, accumulates in the chamber, while plasma and lighter particles, such as platelets, flow past the proximal end 298 of the rod and out the outlet 116. When a sufficient quantity of the heavier particles has accumulated in the chamber, the speed of the rotor is reduced and the spring 308 presses the rod against the outlet 116, as shown in FIG. 10. The distal end 296 of the rod 292 disengages from the cup 300, opening the lumen 294. The heavier particles are pushed through the lumen and out the outlet 116. Additional fluid continues to enter the chamber through the inlet 118 as the heavier particles are harvested from the distal end of the chamber. As in the first embodiment, this allows the heavier particles to be collected more quickly, without excessive addition of new fluid. It will be observed, that the vents 276 of the first embodiment are closer to the distal end of the separation chamber than is the distal end 296 of the rod 292 of the second embodiment, while the rod 292 of the second embodiment is less complex than the rod 262 of the first embodiment. Each embodiment presents advantages to the skilled artisan.

What is claimed is:

1. A disposable cell separation set comprising
   a fluidized-bed cell separation chamber adapted to be mounted on a centrifugal apparatus, said cell separation chamber having a generally conically main body, said main body being symmetrical around an axis with an inlet at an apex of the conically shaped main body and an outlet centrally located at a base of the main body, and
   an internal gravity valve mounted within said separation chamber and integral with said separation chamber, said gravity valve selectively allowing fluid flow through a first flow path near said inlet to said outlet and alternatively through a second flow path near said outlet of said separation chamber to said outlet.

2. The disposable cell separation set according to claim 1 wherein said gravity valve comprises a rod adapted to be displaced from said outlet toward said inlet centrally positioned around said axis.

3. The disposable cell separation set of claim 2 wherein said rod has a bore extending from a first end of the rod and one or more vents at a stopped end of said bore, whereby said bore and said one or more vents provide a fluid path into said separation chamber.

4. The disposable cell separation set of claim 3 further comprising a pipe extending from said inlet to a location near said vents in said rod, allowing fluid to flow from said inlet, through the pipe, out the vents and into the cell separation chamber.

5. The disposable cell separation set of claim 4 wherein said rod also comprises one or more conduits extending from the distal end to a proximal end of the rod.

6. The disposable cell separation set of claim 5 wherein the conduits are in fluid connection with the interior of the separation chamber through orifices at the first end of the rod and through a cavity at the second end to the rod.

7. The disposable cell separation set of claim 2 further comprising at least one spring acting on the rod of the gravity valve.

8. The disposable cell separation set of claim 2 wherein said rod comprises a lumen extending from a distal end to a proximal end of said rod.

9. The disposable cell separation set of claim 8 wherein said separation chamber further comprises a cup detachably supporting said distal end of said rod, said cup being affixed to said main body of said separation chamber between said inlet and said outlet.

10. The disposable cell separation set of claim 9 wherein said cup is mounted in a disc, said disc having at least one opening therein.

* * * * *